United States Patent [19]

Trauthen

[11] Patent Number: 5,239,982
[45] Date of Patent: Aug. 31, 1993

[54] CATHETER DEPTH GAUGE AND METHOD OF USE

[75] Inventor: Brett Trauthen, Corona del Mar, Calif.

[73] Assignee: Baxter International Inc., Deerfield, Ill.

[21] Appl. No.: 972,071

[22] Filed: Nov. 5, 1992

Related U.S. Application Data

[63] Continuation of Ser. No. 712,238, Jun. 7, 1991, abandoned.

[51] Int. Cl.$^5$ .............................................. A61B 1/00
[52] U.S. Cl. ......................................... 128/4; 604/96; 604/117
[58] Field of Search ..................... 604/117, 96, 97, 98, 604/99, 100, 164; 128/4, 6; 606/194

[56] References Cited

U.S. PATENT DOCUMENTS

| | | | |
|---|---|---|---|
| 2,382,109 | 8/1945 | Sheiffele | 128/4 |
| 3,817,619 | 6/1974 | Kawahara . | |
| 4,033,043 | 7/1977 | Cunningham . | |
| 4,121,572 | 10/1978 | Krzeminski . | |
| 4,271,829 | 6/1981 | Heckele . | |
| 4,331,132 | 5/1982 | Mukasa . | |
| 4,464,175 | 8/1984 | Altman et al. | 604/99 |
| 4,641,912 | 2/1987 | Goldenberg . | |
| 4,645,491 | 2/1987 | Evans | 604/117 |
| 4,702,229 | 10/1987 | Zobel . | |
| 4,726,121 | 2/1988 | Ray et al. . | |
| 4,733,661 | 3/1988 | Palestrant . | |
| 4,762,129 | 8/1988 | Bonzel | 606/194 |
| 4,820,043 | 4/1989 | Diener . | |
| 4,887,605 | 12/1989 | Angeisen et al. . | |
| 4,930,525 | 6/1990 | Palestrant . | |
| 4,945,894 | 8/1990 | Kawashima | 128/6 |
| 4,945,895 | 8/1990 | Takai et al. | 128/6 |
| 4,957,484 | 9/1990 | Murtfeldt | 604/280 |
| 4,961,738 | 10/1990 | Mackin | 128/6 |
| 4,980,763 | 12/1990 | Lia | 128/6 |
| 5,030,227 | 7/1991 | Rosenbluth et al. | 128/4 |
| 5,040,548 | 8/1991 | Yock | 606/194 |

FOREIGN PATENT DOCUMENTS

| | | |
|---|---|---|
| 0050606 | 4/1982 | European Pat. Off. . |
| 0226397 | 12/1986 | European Pat. Off. . |
| 0362494 | 7/1989 | European Pat. Off. . |
| 0352872 | 1/1990 | European Pat. Off. . |
| 2756427 | 6/1979 | Fed. Rep. of Germany . |
| 2379273 | 9/1978 | France . |
| 2035097 | 11/1979 | United Kingdom . |
| 2201783 | 9/1988 | United Kingdom . |

Primary Examiner—John J. Wilson
Assistant Examiner—Jeffrey A. Smith
Attorney, Agent, or Firm—Raymond Sun; Kurt A. MacLean

[57] ABSTRACT

A catheter meter is described for determining spacial parameters such as linear distance in a vessel or other body cavity. The catheter meter includes a catheter having a proximal end and a distal end and a handle for holding the catheter. The catheter further includes a hollow tubular member defining a lumen extending distally of the handle to a catheter tip. A wall in the catheter defines a passageway communicating with the lumen for passing a cylindrical member such as a tube or cable having a length and a tip through the passageway and the lumen so that the tip of the cylindrical member can extend distally of the catheter tip. A measurement gauge at the proximal end of the catheter is provided for measuring the distance from the proximal end of the catheter to the tip of the cylindrical member when the tip has been passed through the catheter passageway and the lumen and beyond the catheter tip.

13 Claims, 3 Drawing Sheets

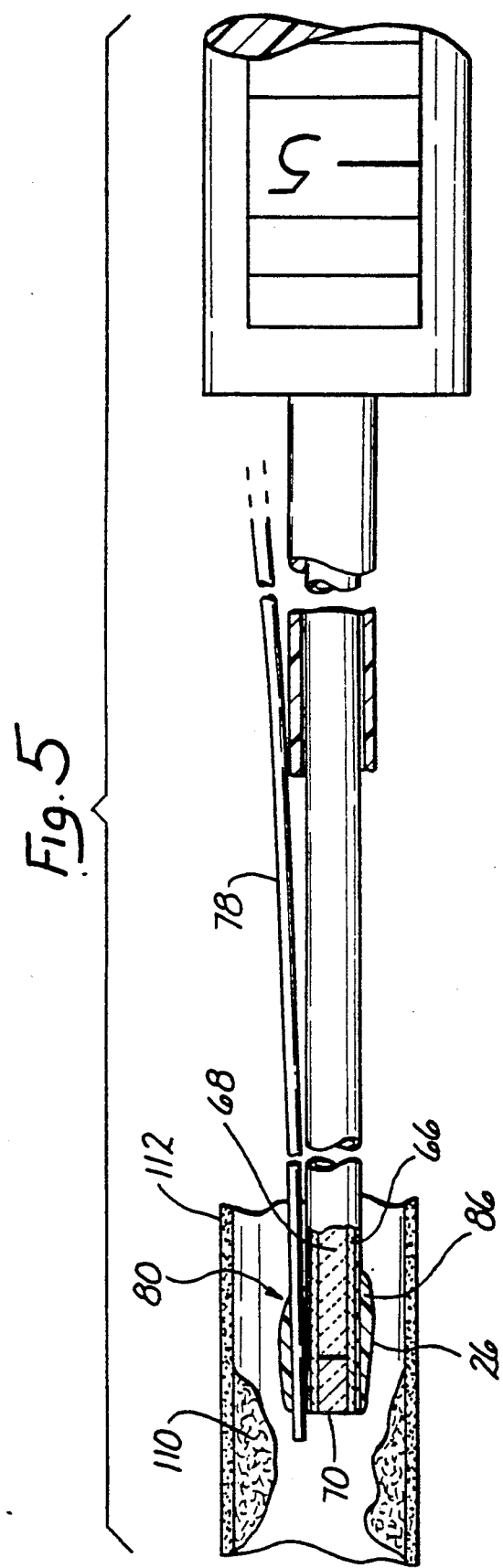

CATHETER DEPTH GAUGE AND METHOD OF USE

This is a continuation of application Ser. No. 07/712,238 filed on Jun. 7, 1991 now abandoned.

BACKGROUND OF THE INVENTION

1. Field of the Invention

The present invention relates in general to the field of catheters for use in exploratory procedures, diagnosis and treatment of biologic conditions, and more particularly, to a catheter meter for determining spacial quantities such as linear distance in a vessel or other comparable environment.

2. Related Art

Catheters are well known in the art and are commonly introduced or inserted into canals, vessels, passageways or body cavities to inspect a region of interest or inject or withdraw fluids from the region or to treat the region, such as to keep a restricted passage open. One medical procedure is known as angioplasty, which has become widely accepted as a safe and effective method for treating various types of vascular diseases. For example, angioplasty has been used for opening stenoses throughout the vascular system, and particularly for opening stenoses in coronary arteries. One common form of angioplasty is called percutaneous transluminal coronary angioplasty. This procedure uses a dilation catheter having an inflatable balloon at is distal end. Using a fluoroscope and radiopaque dyes for visualization, the distal end of the dilation catheter is guided into position across the stenosis and the balloon is inflated for a brief period to reopen the artery and reestablish adequate blood flow.

A number of balloon catheter designs have been developed and have contributed to the safety and acceptability of percutaneous transluminal coronary angioplasty and similar medical procedures. The most common design is known as an "over the wire" balloon catheter. This prior art device typically uses a relatively large lumen for passing a guide wire and injecting angiographic visualization dye to assist in placing the device. A second parallel lumen is provided for inflation and deflation of the balloon. Typically, a steerable guide wire is positioned within the larger lumen and the entire assembly is maneuvered into an initial position within the target artery through a previously positioned large diameter guide catheter. Once near the sight of the stenosis, the guide wire can be rotated and axially extended or retracted into position across the lesion. The catheter is then advanced along the guide wire to position its balloon end across the lesion prior to inflation of the balloon and dilation of the stenosis.

Typically, the vascular stenosis is located and the dilation balloon positioned by fluoroscopy. In that procedure, the radiopaque dyes are injected into the vessel after the catheter has been introduced into the vessel. The stenosis is then located and the end of the catheter is determined relative to the stenosis. The inflatable balloon can then be moved across the stenosis and inflated to open the stenosis. While fluoroscopy is a well accepted procedure and can be properly carried out by an experienced physician, it nonetheless requires injection of the radiopaque dyes and use of x-rays to be able to view the remote area of interest.

Once the stenosis is located, dilating the stenotic lesion requires a substantial effort, which is not always entirely successful. For example, successful treatment requires a properly sized inflation balloon to be placed across the stenosis and inflated to remove the stenosis. Determining the proper balloon size is often difficult and not always correct on the first try, requiring a second procedure with a different sized balloon.

In one procedure for estimating the size of the stenotic lesion, sufficient radiopaque dye must be kept in the vessel to permit viewing by fluoroscope. In order to obtain sufficient information about the stenotic lesion to estimate its size, the patient must be turned through various positions to obtain a series of different views of the vessel. If the patient remains sufficiently immobile, sufficient views of the vessel taken, even though the vessel such as a cardiac artery may be moving, and the radiopaque dye is maintained in the vessel, it is nonetheless difficult to accurately estimate the size and form of the stenotic lesion.

If the inflatable balloon chosen to open the stenotic lesion is too small, the stenosis will not be sufficiently opened, and a larger balloon must be used after the first procedure. If the inflatable balloon is too larger, the vessel may reflexively reconstrict, limiting adequate blood flow through the vessel. Repeated processes result in trauma to the patient and possible harm to the vessel receiving the catheter, thereby increasing the risk of complications. Therefore, it is not only difficult to accurately measure linear distances using catheters but it is also difficult to adequately measure other quantifiable parameter such as size and shape. This inability to adequately measure and quantify unknown quantities and the possibility of repeated procedures may ultimately lead to complications during certain medical procedures.

In the past these duel lumen catheters, however, have been relatively bulky and stiff, making their use difficult for any lesions except those proximal and localized in non-tortuous, easily accessible vessels.

Accordingly, it is an object of the present invention to provide a catheter depth gauge which can measure linear distance from the top or proximal of the catheter device to an object of interest at the distal end.

It is an additional object of the present invention to provide a device which will allow a physician to quantify distances and other spacial parameters in order to provide a reference point for surgery, data for diagnosis and treatment of symptoms and to minimize the number of procedures and steps necessary to achieve the desired result.

It is a further object of the present invention to provide a device which allows a physician to determine the size and extent of conditions such as vascular stenosis for purposes of diagnosis and treatment of vascular disease.

It is an additional object of the present invention to provide a device which allows a physician to determine which vascular areas of a particular vessel should be treated and which areas may be passed over. These and other objects are achieved by the device of the present invention.

SUMMARY OF THE INVENTION

In accordance with the present invention, a catheter combination is provided which allows measurement of such spacial parameters as linear distance and size of an object of interest in a vessel or body cavity from the proximal end of the catheter, thereby minimizing the number of procedures required to quantify, diagnose and treat the condition under consideration. The catheter combination includes a catheter having a lumen extending distally to a catheter tip. The catheter combination further includes a wall in the catheter defining a passageway communicating with the lumen for passing a suitably shaped and sized member such as a tube, fiber bundle or cable, such as for an endoscope, through the passageway and the lumen so that the tip of the member can extend distally from the catheter tip. The catheter combination further includes means at the proximal portion of the catheter for measuring the distance from the proximal portion of the catheter to the tip of the member when the tip has been passed through the catheter passageway and the lumen and beyond the catheter tip.

This catheter combination allows the physician to measure the linear distance from the proximal end of the catheter to the tip of the member, such as a tube, bundle or cable, extending through the lumen and beyond the end of the catheter. The physician can then measure the linear distance to an object of interest and other spacial parameters relating to the object. Qualitative information about the object obtained through the present invention can then be used to diagnose and treat conditions, for example vascular stenosis and the like. The number of procedures necessary to achieve the desired treatment are minimized, and potentially undesirable procedures such as use of x-rays for fluoroscopy can be minimized or even in some cases eliminated.

In one form of the invention, the measuring means of the catheter combination includes a transparent gauge means in a handle having a scale so that pre-applied visible markings on a cylindrical member, such as an angioscope or other endoscope bundle passed through the passageway, can be viewed through the transparent gauge means and compared with the scale to determine the length of the bundle extending between the graduations and the tip of the angioscope bundle. The gauge means can be used to measure the distance the bundle extends beyond the catheter tip or the distance from the tip of the bundle to the object of interest. For example, the tip of the bundle can be advanced to the object of interest and then retracted a desired distance, such as the distance necessary to place the object in focus. The distance between the bundle tip and the object of interest is then quantifiable through the gauge means. The distance from the tip of the bundle to the object, along with other quantitative information available to the physician can then be used to determine the size of the object.

In a further form of the invention, an occlusion catheter having an occlusion cuff at the tip is used with radiopaque markers on the tip of the catheter and on the tip of the angioscope bundle to provide additional information during any fluoroscopy which may be done.

In operation, the catheter combination is introduced into the vessel or body cavity of interest and positioned as desired. A suitable guide wire may be used to properly introduce and position the catheter combination. The occlusion cuff may be inflated to block the flow of fluid around the object of interest, and any residual fluid may be flushed, with a saline solution for example, to permit adequate viewing of the object. The distance from the end of the scale to the tip of the catheter is already known since the catheter handle and the catheter tube are of a known length. The distance which the angioscope tip extends beyond the end of the catheter is quantified by viewing markings on the angioscope bundle relative to the scale on the transparent gauge in the handle of the catheter, perhaps also while viewing the object through the angioscope and monitor. To develop information about the object of interest, such as a stenotic lesion, the tip of the angioscope may be advanced into contact with the stenotic lesion. If the stenosis is small enough to still allow passage of the angioscope through it, the angioscope may be passed across the stenotic legion. By estimating with the angioscope the location of the distal end of the lesion, and thereafter withdrawing the angioscope to the estimated location of the proximal end of the stenosis, an estimate of the length of the stenosis can be made by noting the locations of the bundle marking relative to the transparent gauge when the angioscope tip is at the distal and proximal portions of the stenosis. The size of the stenosis can be approximated by noting on the transparent gauge means the location of the proximal end of the stenosis, and then further withdrawing the angioscope until the stenosis is in full focus and noting on the transparent gauge means the location of the angioscope tip.

Other features and advantages of the present invention will become apparent from the following detailed description of the preferred embodiments taken in conjunction with the accompanying drawings which illustrate, by way of example, principles of the present invention.

BRIEF DESCRIPTION OF THE DRAWINGS

FIG. 5 is a fragmentary and partial cut-away top plan view of the catheter combination of FIG. 1 showing an endoscope in a vessel.

DETAILED DESCRIPTION OF THE PREFERRED EMBODIMENTS

Figure 1:
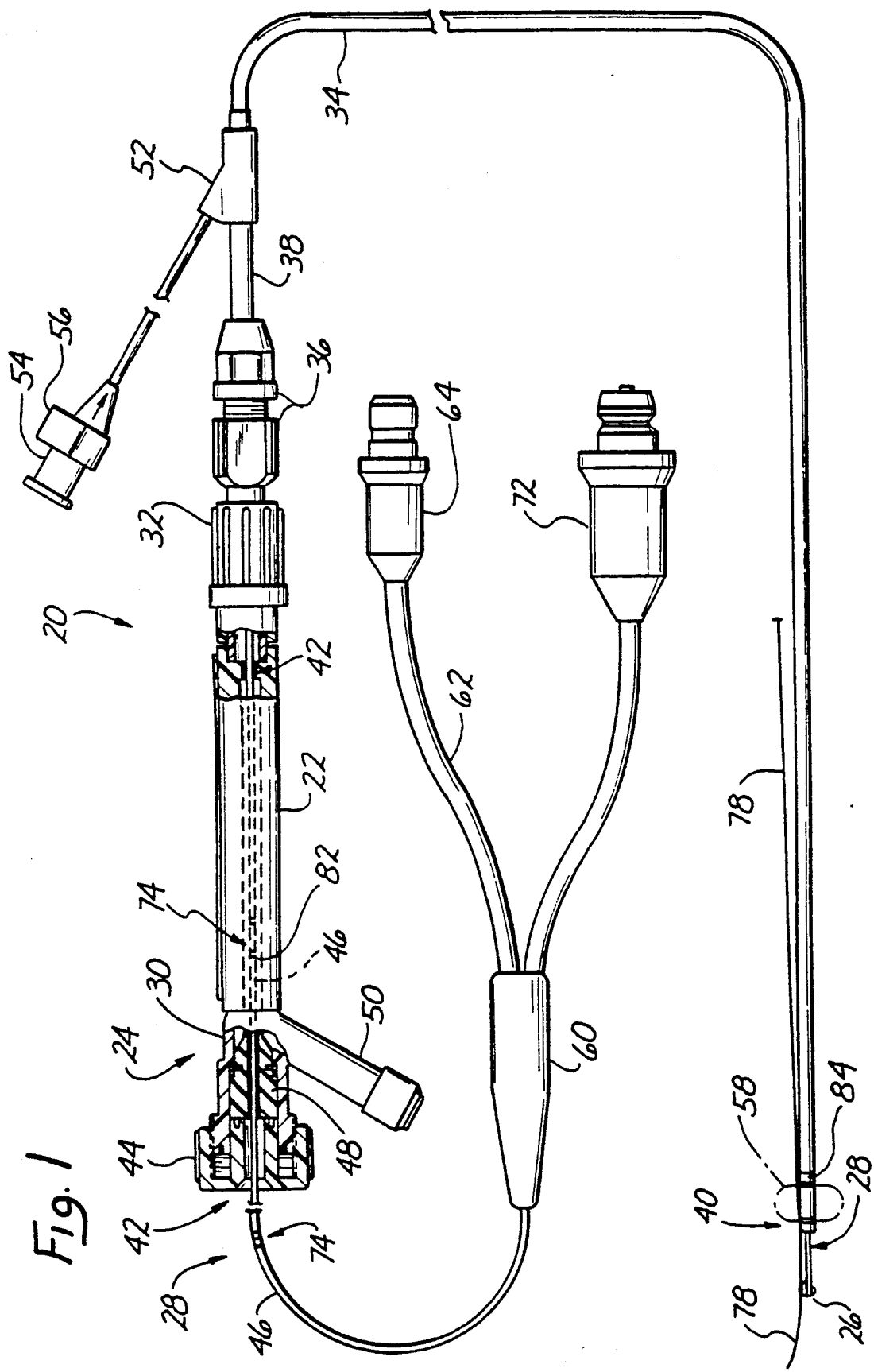
FIG. 1 is a partial cut-away plan view of a catheter combination in accordance with one form of the present invention.
Figure 2:
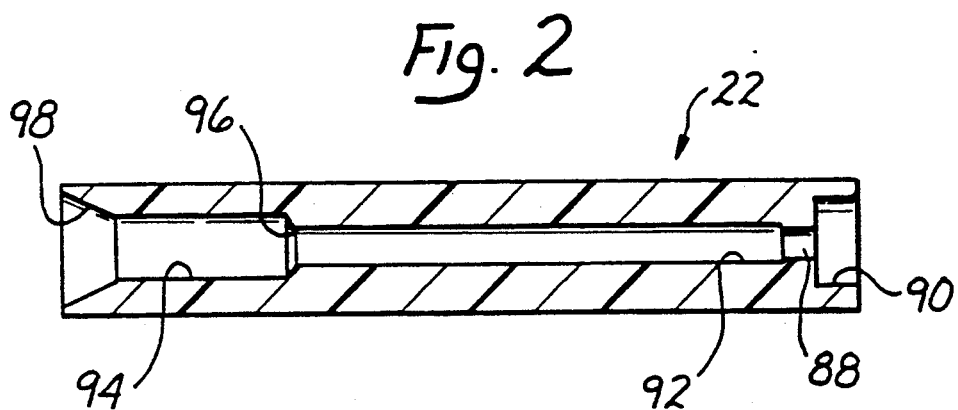
FIG. 2 is a top longitudinal sectional view of a transparent gauge means in the catheter combination of FIG. 1.

In accordance with the invention, the improved catheter assembly 20 (FIG. 1) allows a physician to determine quantitative spacial parameters regarding an object of interest in a vessel or body cavity, thereby allowing the physician to more effectively analyze, diagnose and treat conditions. The catheter combination minimizes the number and extent of procedures necessary to quantify information about an object of interest and minimizes the possibility of repeated procedures to effect any necessary diagnosis and treatment. The catheter combination 20 of the present invention includes a transparent gauge 22 at a proximal end 24 of the catheter for measuring the distance from the proximal end of the catheter to the tip 26 of a cylindrical member such as an angioscope 28. The transparent gauge 22 may also serve as a handle for the catheter coupled between a Y-connector 30 and a rotating adaptor 32, elements that are well known to those skilled in the art. A flexible catheter tube 34 is mounted to the rotating adaptor through a catheter hub 36 and a barrel 38.

The catheter tube 34 is hollow and defines a first or primary lumen extending distally of the proximal end to a catheter tip 40. The lumen is confluent with a passageway 42 in the proximal end of the catheter beginning at a Y-connector cap 44 and extending through the Y-connector 30, the transparent gauge 22, the rotating adapter 32, catheter hub 36 and the barrel 38. The passageway accepts a cylindrical member such as the fiber optic bundle 46 of the angioscope 28 to be fed into the primary lumen of the catheter tube 34. The passageway 42 is defined by the internal walls of those components at the proximal end of the catheter.

Upon initial assembly, the fiber optical bundle is passed through the Y-connector cap 44 and through a packing element in the form of dynamic seal 48 which closes off the Y-connector to fluid being injected through the irrigation duct 50, which admits fluid from the duct into the same passageway containing the fiber optic bundle. After the Y-connector, the fiber optic bundle is threaded through a preferably coaxial channel through the transparent gauge 22, and then passed through a preferably coaxial passageway through the rotating adapter 32 and the catheter hub 36 into the barrel 38. The fiber optical bundle is then fed through the primary lumen of the flexible catheter tube 34 until the tip 26 of the fiber optic bundle emerges from the catheter tip 40. The catheter tube 34 is sized sufficiently larger than the outside diameter of the fiber optic bundle to allow passage of fluid through the primary lumen from the irrigation duct 50. The catheter tube 34 includes a secondary, balloon inflation lumen connected through a Y-junction 52 to a cuff inflation connector 54 having a gate valve 56. The cuff inflation connector is used to inflate an occlusion cuff 58.

The proximal end of the fiber optic bundle 46 includes an optic junction 60 which connects a light bundle to a series of cylindrically arranged optic fibers for supplying light from a light connector 64 to the cylindrically arranged optic fibers. These optic fibers extend the length of the fiber optic bundle to the tip 26 and have ends exposed at the tip for transmitting the light beyond the tip of the fiber optic bundle. The optic fibers 66 surround the primary optic bundle 68 (shown schematically in FIG. 5) for transmitting light received by the lens 70 back through the fiber optic bundle to an image connector 72. The light connector 64 may be coupled to a suitable light cable and light source (not shown), while the image connector may be coupled to an appropriate focusing coupler, remote head, camera processor, video tape recorder and monitor, as necessary.

Figure 3:
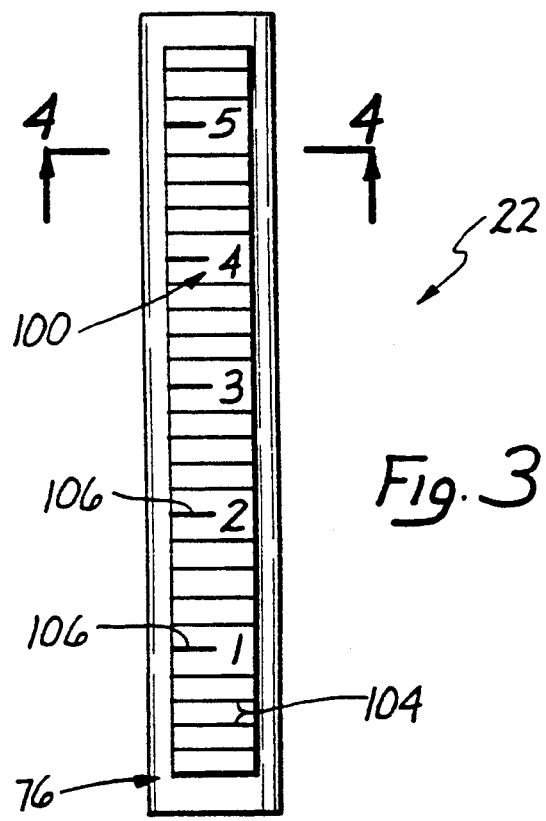
FIG. 3 is a top plan view of the transparent gauge means in the handle of the catheter combination of FIG. 1.

The fiber optic bundle 46 further includes discrete markings 74 formed in or placed on the outer surface of the fiber optic bundle to be viewed through the transparent gauge 22 as appropriate portions of the bundle pass through the gauge 22. The markings 74 are placed at locations on the bundle at known and predetermined distances from the tip 16 of the fiber optic bundle. In one preferred embodiment, one discrete and identifiable marking on the fiber optic bundle will coincide with the zero mark 76 on the transparent gauge (FIG. 3) when the tip 26 of the fiber optic bundle is a short, predetermined distance beyond the catheter tip 40. The distance which the fiber optic bundle tip extends beyond the catheter tip 40 is sufficient to allow a flexible guide wire 78 external to the catheter to be threaded to an orifice 80 in the tip 26 (FIG. 5). One such mark is shown at 82 (FIG. 1).

The catheter tip preferably includes a radiopaque marker 84, and the tip 26 of the fiber optic bundle preferably includes a similar radiopaque marker 86 formed from a suitable metal, as known to those skilled in the art, so that the relative locations of the catheter tip and the angioscope tip can be viewed using a fluoroscope.

The transparent gauge 22 is made from a suitable clear plastic material such as polycarbonate and includes a first bore 88 defining the smallest diameter of the passageway through the transparent gauge 22. A mating counterbore 90 is formed at the distal end of the transparent gauge to accept the male fitting of the rotating adaptor 32 (FIG. 1) to form a friction fit, fluid-tight connection. An intermediate counterbore 92 extends proximally of the first bore 88 along a substantial portion of the length of the transparent gauge 22. A second mating counterbore 94 connects the intermediate counterbore 92 through a countersink 96 to a frustoconical section 98 for mating with the distal end of the Y-connector 30. The Y-connector 30 fits into the second mating counterbore 94 to form a fluid-tight seal between the Y-connector and the transparent gauge.

Figure 4:
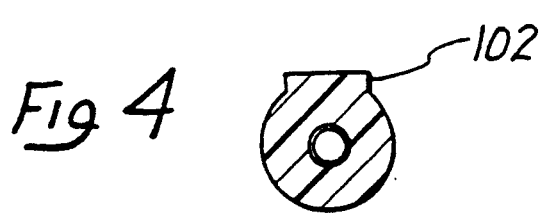
FIG. 4 is a transverse cross-sectional view of the transparent gauge means taken along line 4—4 of FIG. 3.

The top portion of the transparent gauge includes a graduated scale 100 (FIG. 3) formed in a gauge window 102 (FIG. 4). The scale includes graduations of a dimension and accuracy appropriate for the particular application for which the catheter combination is to be used. For example, the individual lines 104 between each integer are preferably 0.010-0.015 inches wide and 2 millimeters apart. The integer scale lines 106 are preferably 0.015-0.020 inches wide, and 10 millimeters apart. The scale shown in FIG. 3, therefore, ranges from 0 to 56 millimeters. The scale can also be shorter, for example running to 54 millimeters or longer, depending upon the application.

To introduce and use the catheter combination 20 in a vessel or body cavity, for example the guide wire 78 is inserted into the target cavity or blood vessel, such as a brachial artery or ilial artery as is known to those skilled in the art. For angiography, using an angioscope 28, the guide wire 78 is introduced upward into a desired vessel of the cardiac artery until it reaches the desired location. The proximal end of the guide wire external to the patient's body is then threaded through the orifice 80 of the angioscope tip 26 of the pre-assembled catheter combination, where the tip 26 is extending slightly beyond the catheter tip 40. The catheter tip 40 extends distally and the angioscope also extends distally known lengths from the zero point 76 on the transparent gauge 22, and the mark 82 on the fiber optic bundle preferably aligns with the zero mark 76 on the transparent gauge. When the assembly is introduced into a vessel in this configuration, the tip 26 of the angioscope extends a known distance into the patient's vessel. When the catheter and angioscope are in place, and the occlusion cuff inflated if necessary, the physician can begin the procedure to diagnose and/or treat the condition.

In order to measure the linear distance from a stenotic lesion to the proximal end of the catheter or to the catheter tip 40, the angioscope 28 (FIG. 5) is fed forward through the lumen of the catheter until the angioscope tip 26 reaches a stenotic lesion, such as that at 110, in the vessel 112. The physician will know that the lesion has been reached by one of several different ways. First, the physician may scan the vessel using a fluoroscope and radiopaque dyes to locate the stenotic lesion and to locate the angioscope tip 26 and catheter tip 40 relative to the lesion. In a second method, the physician may observe the image from the angioscope while advancing the angioscope. When the physician believes that the tip of the angioscope is approaching a stenosis, the angioscope can be advanced until the tip 26 is adjacent the stenosis 110. The physician then reads the transparent gauge to note the location of the mark 82 relative to the scale on the transparent gauge. In a third method applicable to severely occluded stenoses, the angioscope can be advanced until the tip of the scope physically reaches the stenosis and can advance no further. The location of the mark 82 is then noted on the transparent gauge. The distance from the proximal end of the catheter to the lesion is then the sum of the previously known distance from the mark 82 to the angioscope tip 26 and the distance the mark 82 has moved along the graduated scale after the angioscope tip 26 has been moved to the stenotic lesion. The result is a measure of the distance from the stenotic lesion, the object of interest, to the proximal end of the catheter.

With the catheter combination 20 described herein, a reference plane is provided which is coincident with the proximal end of the catheter at the zero mark 76 from which a plurality of measurements can be made. Measurements can be taken of the locations of various stenotic lesions, all using the same reference point. Other information can also be gathered, such as the length of each lesion and other quantitative information about the shape of the stenotic lesion. The ability to make these measurements allows a physician to reliably and accurately determine the position and characteristics of the object of interest, thereby minimizing repetitious and possibly undesirable procedures. The physician need no longer rely exclusively on qualitative, magnified information such as is developed through fluoroscopy. The reference point provided by the end of the catheter combination provides a reliable reference point for subsequent treatment using currently established procedures.

While the catheter combination may take several configurations, some exemplary dimensions will be given for purposes of discussion. For example, in an angioscope application, the catheter tube is preferably a 4.5 F catheter, and accepts a 0.6 millimeter outside diameter fiber optic bundle through the primary lumen of the catheter. The lumen for inflation of the occlusion cuff is of a suitable size to properly inflate the cuff. The inside diameter of the primary lumen is sufficient to allow irrigation and injection of fluids, for example saline, radiopaque dyes or medication, within the primary lumen and around the fiber optic bundle. The radiopaque marker 86 on the angioscope tip is preferably a gold marker extending completely around the outer polyvinyl chloride tubing of the optic fiber bundle. The tip 26 is preferably a formed polyvinyl chloride tip fixed to the outside end of the optic fiber bundle tubing through an acrylic ester, ultraviolet-cured adhesive. The outer polyvinyl chloride tubing for the bundle encloses the cylindrically arranged polymethyl methacrylate light fibers 66 used for transmitting light from an OPTX 300 light source, capable of converting 300 watts of electrical power into more than 100,000 LUX (lumens per square meter). The light fibers 66 are set in epoxy potting adhesive around the lens and image fiber bundle. The lens 70 is preferably a glass gradient index lens sealed to the distal end of the silica image fiber bundle 68 by an acrylic ester ultraviolet-cured adhesive. The lens is preferably designed to have a magnification of 1/10 at 5 millimeters. The monitor coupled through various electronics to the image connector 72 is typically a viewing monitor such as those presently used in angiography. The magnification for images transmitted through an angioscope for a 13 inch screen is typically 240.

With the knowledge of the lens characteristics and of the particular viewing monitor used with the system, the physician can obtain additional data regarding the shape of the object of interest. For example, the size of a vascular stenosis can be determined by measuring the transverse dimensions on the viewing monitor. By one method, the tip of the angioscope, at which the lens is located, is advanced to the point of the vascular stenosis. The angioscope is then pulled back 5 millimeters, or until the stenosis comes into focus. Knowing the magnification at 5 millimeters, or knowing the magnification of the lens at the final distance the angioscope was withdrawn to bring the stenosis into focus, and knowing the magnification of the viewing monitor, the size of the stenosis can be measured on the monitor. The size of the stenosis on the monitor is divided by 240, the magnification of the monitor, and divided by the magnification of the lens to arrive at the actual dimensions of the stenotic lesion. With this significant information, the physician can determine whether or not angioplasty or some other treatment is necessary, and if so, the size of the inflatable balloon or other instrument necessary to adequately treat the stenotic lesion. Thus, the number of diagnostic and treatment procedures necessary are minimized once the linear distance of an object in a vessel or other body cavity can be measured.

Therefore, the catheter combination as disclosed provides an apparatus allowing measurement of spacial parameters such as linear distance and size of an object in a vessel or body cavity from the proximal end of the apparatus. Armed with such information, the physician can make a more informed decision as to whether or not to treat the particular condition, and if so what the best procedure for treatment is. Therefore, the risk of complications and any unnecessary trauma is minimized.

It is to be understood that the embodiments of the invention disclosed herein are illustrative of the principles of the invention and that other modifications may be employed which are still within the scope of the invention. Accordingly, the present invention is not limited to those embodiments precisely shown and described in the specification but only by the following claims.

I claim:

1. A catheter meter for determining linear distance in a vessel or body cavity, the catheter meter comprising:
   a catheter having a proximal end and a distal end and including a hollow body and a hollow tubular member defining a lumen joining and extending distally of the body to a catheter tip and an occlusion cuff and a radiopaque marker at the catheter tip;
   an angioscope having a length, a distal tip with an aperture in the distal tip and an outer wall with at least one marking on the outer wall extending through the hollow body and the lumen so that the distal tip of the angioscope extends distally of the catheter tip;
   transparent gauge means in the body at the proximal end of the catheter to allow viewing of the marking on the outer wall of the angioscope through the transparent gauge means and having a scale for measuring the length of the angioscope that has passed through the hollow body past the transparent gauge means;

means for injecting fluid through the lumen and around the angioscope to the catheter tip; and a guide wire passing through the aperture and external to the catheter.

2. The catheter meter of claim 1 wherein the angioscope further comprises a proximal end, an image connector at the proximal end of the angioscope, a light collecting lens at the distal tip of the angioscope, and optical fibers for transmitting collected light back to the image connector.

3. The catheter meter of claim 2 wherein the angioscope is movable within the lumen and further includes a radiopaque marker on the distal tip thereof.

4. The catheter meter of claim 2 wherein:

the outer wall of the angioscope encloses the optical fibers;

the outer wall extends from the proximal end of the angioscope; and the at least one marking on the outer wall includes spaced markings visible through the transparent gauge means to indicate in combination with the scale on the gauge means how far the distal tip of the angioscope extends beyond the catheter distal end.

5. A method for determining spacial parameters such as the linear distance from an object of interest within a body cavity or vessel, the method comprising the steps of:

introducing into a body area to be examined a catheter having a proximal end and a distal end and including a hollow body and a hollow tubular member defining a lumen joining and extending distally of the body to a catheter tip;

moving a cylindrical member having an outer wall with at least one marking on the outer wall and extending through the lumen of the catheter so that the tip of the cylindrical member extends distally of the catheter tip so as to move the tip of the cylindrical member away from the catheter tip and adjacent to the object of interest;

comparing a marking on the outer wall of the cylindrical member with a transparent gauge in the body of the catheter at the proximal end of the catheter to record a first location of the marking relative to the gauge when the tip of the cylindrical member is adjacent the object of interest;

moving the tip of the cylindrical member away from the object of interest;

comparing the marking on the wall of the cylindrical member with the transparent gauge to record a second location of the marking relative to the gauge; and measuring the distance between the first and second locations representing the linear distance between the object of interest and the tip of the cylindrical member.

6. The method of claim 5 including the step of determining when the tip of the cylindrical member is adjacent the object of interest.

7. The method of claim 6 including the step of visualizing the object of interest.

8. The method of claim 5 further comprising the step of determining the size of the object of interest.

9. The method of claim 5 further comprising the steps of: focusing the object of interest to record the second location; and determining the size of the object of interest.

10. The method of claim 5 further comprising the step of inflating an occlusion cuff on the tip of the catheter to fix the catheter in the body region.

11. The method of claim 5 further comprising the step of moving the catheter along a guide wire external to the catheter passing through an aperture on the tip of the cylindrical member.

12. A method for determining spacial parameters such as linear distance in a body cavity or vessel, the method comprising the steps of:

introducing into a body area to be examined a catheter having a proximal end and a distal end and including a hollow body and a hollow tubular member defining a lumen joining and extending distally of the body to a catheter tip;

providing an endoscope having an image lens for viewing an object in the body region, means for emitting light from a tip of the endoscope and a light transmitting bundle for transmitting collected light to the proximal end of the catheter, the endoscope further having an outer wall with at least one marking on the outer wall;

extending the endoscope through the lumen of the catheter so that the tip of the endoscope extends distally of the catheter tip;

moving the tip of the endoscope away from the catheter tip and closer to an object of interest;

observing the location of the marking on the endoscope outer wall relative to a transparent gauge in the body of the catheter at the proximal end of the catheter;

moving the endoscope in the opposite direction while viewing an image of the object of interest;

observing the location of the marking on the endoscope outer wall relative to a transparent gauge in the body of the catheter at the proximal end of the catheter;

moving the endoscope in the opposite direction while viewing an image of the object of interest;

discontinuing movement of the endoscope when the object of interest is in focus; and comparing the marking on the endoscope outer wall with the transparent gauge to measure the length of the endoscope that has passed through the hollow body past the transparent gauge.

13. The method of claim 12 further comprising the step of determining the size of the object of interest.

* * * * *